US011311660B2

(12) United States Patent
Holigan et al.

(10) Patent No.: US 11,311,660 B2
(45) Date of Patent: Apr. 26, 2022

(54) UTERINE DISTENSION FLUID MANAGEMENT SYSTEM AND METHOD

(71) Applicant: HOLOGIC, INC., Marlborough, MA (US)

(72) Inventors: David J. Holigan, Marlborough, MA (US); Joanna Myczkowska, Marlborough, MA (US); William Lucas Churchill, Marlborough, MA (US); Danny Macari, Marlborough, MA (US)

(73) Assignee: Hologic, Inc., Marlborough, MA (US)

(*) Notice: Subject to any disclaimer, the term of this patent is extended or adjusted under 35 U.S.C. 154(b) by 137 days.

(21) Appl. No.: 16/645,372

(22) PCT Filed: Jul. 31, 2019

(86) PCT No.: PCT/US2019/044443
§ 371 (c)(1),
(2) Date: Mar. 6, 2020

(87) PCT Pub. No.: WO2020/033209
PCT Pub. Date: Feb. 13, 2020

(65) Prior Publication Data
US 2020/0297900 A1 Sep. 24, 2020

Related U.S. Application Data

(60) Provisional application No. 62/716,300, filed on Aug. 8, 2018.

(51) Int. Cl.
*A61M 1/00* (2006.01)

(52) U.S. Cl.
CPC ......... *A61M 1/777* (2021.05); *A61M 2205/18* (2013.01); *A61M 2205/3393* (2013.01);
(Continued)

(58) Field of Classification Search
CPC .............. A61M 1/777; A61M 2205/18; A61M 2205/3341; A61M 2205/3393;
(Continued)

(56) References Cited

U.S. PATENT DOCUMENTS 5,709,670 A * 1/1998 Vancaillie ........... A61M 3/0212
604/246

FOREIGN PATENT DOCUMENTS

WO    WO 97/16220 A1    5/1997
WO    WO 2007/124069 A2    11/2007

OTHER PUBLICATIONS

PCT International Search Report for PCT/US2019/044443, Applicant: Hologic, Inc., Form PCT/ISA/210 and 220, dated Jan. 27, 2020 (9 pages).

(Continued)

*Primary Examiner* — Deanna K Hall
(74) *Attorney, Agent, or Firm* — Vista IP Law Group, LLP (57) ABSTRACT

A method for operating a fluid management system includes automatically detecting an unstable condition in the system, which may include detecting a large change in the supply fluid amount (indicative of a bag change), detecting a large change in the waste fluid amount (indicative of a bag change), or detecting a large difference between the amount of fluid dispensed as measured by the weight data and the amount of fluid dispensed as measured by the flow data (indicative of a blockage in the supply tubing). The method further includes adjusting the operating mode of the system during the unstable condition, which may include switching to using flow data rather than weight data to track the fluid deficit during a supply bag exchange, halting operation of an
(Continued)

outflow pump during a waste container exchange, and/or halting operation of the system during a blockage in the supply tubing.

12 Claims, 5 Drawing Sheets

(52) U.S. Cl.
CPC ... *A61M 2205/50* (2013.01); *A61M 2205/581* (2013.01); *A61M 2205/583* (2013.01)

(58) Field of Classification Search
CPC ...... A61M 2205/50; A61M 2210/1433; A61M 3/0208; A61M 3/022; A61M 3/0258; A61M 3/0212
See application file for complete search history.

(56) References Cited

OTHER PUBLICATIONS

PCT Written Opinion of the International Search Authority for PCT/US2019/044443, Applicant: Hologic, Inc, Form PCT/ISA/237, dated Jan. 27, 2020 (12 pages).
Foreign Response for EP Patent Appln. No. 19762245.9 dated Sep. 27, 2021.

* cited by examiner

UTERINE DISTENSION FLUID MANAGEMENT SYSTEM AND METHOD

RELATED APPLICATIONS DATA

The present application is a National Phase entry under 35 U.S.C § 371 of International Patent Application No. PCT/US2019/044443, having an international filing date of Jul. 31, 2019, which claims the benefit under 35 U.S.C. § 119 to U.S. Provisional Patent Application Ser. No. 62/716,300, filed Aug. 8, 2018, which is incorporated by reference in its entirety into the present application.

FIELD

The present disclosure generally relates to a fluid management system and method for tracking the fluid deficit using the fluid management system, and more specifically, to a fluid management system that includes load cells for measuring the supply fluid weight and the waste fluid weight so that, when there is a disturbance in the system, the operating conditions of the system may be automatically adjusted in order to more accurately track the fluid deficit.

BACKGROUND

Uterine fibroids are well-defined, non-cancerous tumors that are commonly found in the smooth muscle layer of the uterus. In many instances, uterine fibroids can grow to be several centimeters in diameter and may cause symptoms like menorrhagia (prolonged or heavy menstrual bleeding), pelvic pressure or pain, and reproductive dysfunction. Current treatments for uterine fibroids include hysteroscopic resection, which involves inserting a hysteroscope (i.e., an imaging scope) into the uterus transcervically (i.e., through the vagina), and then cutting away the fibroid from the uterus using a tissue removal device delivered to the fibroid via a channel in the hysteroscope.

In hysteroscopic resection procedures, prior to fibroid removal, the uterus is typically distended to create a working space within the uterus. Such a working space does not normally exist in the uterus because the uterus is a flaccid organ. As such, the walls of the uterus are typically in contact with one another when in a relaxed state. The conventional technique for creating such a working space within the uterus is to administer a fluid to the uterus through the hysteroscope under sufficient pressure to cause the uterus to become distended.

Examples of the fluid used conventionally to distend the uterus include gases like carbon dioxide or, more commonly, liquids like water or certain aqueous solutions, e.g., a saline or other physiologic solution or a sugar-based or other non-physiologic solution. Because the distending fluid is administered under pressure, which may be as great as 100 mm Hg or greater, there is a risk, especially when vascular tissue is cut, that the distending fluid may be taken up by blood vessel(s) in the uterus, referred to as "intravasation," which may be harmful to the patient if too much of the distension fluid is taken up.

Thus, during a procedure involving fluid distension of the uterus, it is customary to monitor the fluid uptake on a continuous basis using a scale system in order to ensure that the patient is not at risk due to excessive intravasation. However, the scale system may become inaccurate and/or unreliable during a disruption, such as during a change of supply fluid bag or waste fluid container, or during a blockage (such as an air bubble) in the supply fluid tubing.

Fluid uptake may alternatively be measured based on the rate of fluid flowing into the patient and the rate of fluid flowing out of the patient. However, small errors in the measured rate can produce large errors in the calculation of the total fluid deficit over time. Therefore, this approach does not provide an accurate measurement of fluid retention of a patient.

Despite the risks of intravasation, with proper monitoring of fluid uptake, hysteroscopic resection is a highly effective and simple technique for removing uterine fibroids. There is a need, however, for a more accurate and reliable procedure for tracking the fluid deficit during hysteroscopic resection.

SUMMARY

One embodiment of the present invention is directed to a method for operating a fluid management system that includes a weighing device. The weighing device may be a supply fluid weighing device configured for weighing a supply fluid container. The weighing device may include one or more load cells. The method includes operating the fluid management system in a first operating mode; obtaining a first weight measurement from the weighing device, wherein the first weight measurement corresponds to an amount of fluid in a fluid container at a first moment in time; obtaining a second weight measurement from the weighing device, wherein the second weight measurement corresponds to an amount of fluid in the fluid container at a second moment in time following the first moment in time; comparing the second weight measurement to the first weight measurement; determining that the fluid management system is in an unstable condition based on the comparison between the second weight measurement and the first weight measurement; and adjusting operation of the fluid management system to operating the fluid management system in a second mode after determining the unstable condition. Operating the fluid management system in the second mode includes receiving flow data from a pump fluidly coupled to the fluid container; and using the flow data to calculate a fluid deficit during the unstable condition.

In one aspect, the method may further include obtaining a third weight measurement from the weighing device, wherein the third weight measurement corresponds to an amount of fluid in the fluid container at a third moment in time following the second moment in time; obtaining a fourth weight measurement from the weighing device, wherein the fourth weight measurement corresponds to an amount of fluid in the fluid container at a fourth moment in time following the third moment in time; comparing the fourth weight measurement to the third weight measurement; determining that the fluid management system is in a stable condition based on the comparison between the fourth weight measurement and the third weight measurement; and adjusting operation of the fluid management system to operating the fluid management system in the first mode after determining the stable condition. Adjusting operation of the fluid management system to operating in the first mode may include switching from using the flow data to calculate the fluid deficit to using weight data received from the weighing device to calculate the fluid deficit.

Another embodiment of the present invention is directed to a method for operating a fluid management system. The method includes operating an inflow pump to pump fluid out of a supply fluid container; obtaining a plurality of supply fluid weight measurements during a predetermined time period from a weighing device (e.g., a load cell) coupled to the supply fluid container while the inflow pump dispenses fluid from the supply fluid container; obtaining a plurality of inflow pump measurements during the predetermined time period from a measuring device coupled to the inflow pump; calculating a first amount of fluid dispensed during the predetermined time period based on the obtained inflow pump measurements; calculating a second amount of fluid dispensed during the predetermined time period based on the obtained supply fluid weight measurements; comparing the first amount to the second amount; determining that a difference between the first amount and the second amount exceeds a predetermined difference limit; and transmitting a visual or audible notification indicating a tubing error upon determining that the difference between the first amount and the second amount exceeds the predetermined difference limit. The method may further include halting operation of the inflow pump upon determining that the difference between the first amount and the second amount exceeds the predetermined difference limit.

Yet another embodiment of the present invention is directed to a fluid management system that includes a supply fluid weighing device configured for weighing a supply fluid container. The supply fluid weighing device may include one or more load cells. The fluid management system further includes an inflow pump configured to pump fluid out of the supply fluid container and a processor coupled to the supply fluid weighing device and the inflow pump. The processor is configured to determine whether the system is in a stable condition or an unstable condition and operate the system according to a first set of operating conditions during the stable condition. The first set of operating conditions may include using weight data obtained from the supply fluid weighing device to calculate a fluid deficit. The processor is further configured to operate the system according to a second set of operating conditions during the unstable condition. Operating the fluid management system according to the second set of operating conditions comprises receiving flow data from the inflow pump; and using the flow data to calculate the fluid deficit during the unstable condition. The processor may be further configured to: obtain a first weight measurement from the supply fluid weighing device; obtain a second weight measurement from the supply fluid weighing device after obtaining the first weight measurement; determine a difference between the second weight measurement and the first weight measurement; and determine whether the system is in the stable condition or the unstable condition based on the difference between the second weight measurement and the first weight measurement. The processer may be further configured to determine that the system is in the stable condition if the difference between the second weight measurement and the first weight measurement is within a predetermined limit. Still further, the processor may be configured to determine that the system is in the unstable condition if the difference between the second weight measurement and the first weight measurement exceeds the predetermined limit.

Still another embodiment of the present invention is directed to a method for operating a fluid management system. The fluid management system includes a supply fluid weighing device, an inflow pump configured to pump fluid out of a supply fluid container, a waste fluid weighing device, an outflow pump configured to pump fluid into a waste fluid container, and a processor operatively coupled to the supply fluid weighing device, the waste fluid weighing device, the inflow pump and the outflow pump, respectively. The method includes determining whether the fluid management system is in a stable condition or an unstable condition, and operating the fluid management system under a first set of operating conditions during the stable condition. The first set of operating conditions may include calculating a fluid deficit based on respective weight measurements received from the supply fluid weighing device and the waste fluid weighing device. The method further includes operating the fluid management system under a second set of operating conditions during the unstable condition. The second set of operating conditions is different from the first set of operating conditions. Operating the fluid management system under the second set of operating conditions includes receiving flow data from the inflow pump, and using the flow data to calculate the fluid deficit during the unstable condition. Determining whether the system is in the stable condition or the unstable condition may include: receiving a current weight measurement from the supply fluid weighing device; comparing the current weight measurement to a previous weight measurement received from the supply fluid weighing device; and determining that the system is in the stable condition if the difference between the current weight measurement and the previous weight measurement is within a predetermined limit. The method may further include determining that the system is in the unstable condition if the difference between the current weight measurement and the previous weight measurement exceeds the predetermined limit.

Yet another embodiment of the present invention is directed to a method for operating a fluid management system. The fluid management system includes a weighing device and a pump. The method for operating the fluid management system includes operating the fluid management system in a first operating mode, wherein operating the fluid management system in the first mode comprises using weight data received from the weighing device to calculate a fluid deficit. The method further includes determining that the fluid management system is in an unstable condition based on data received from at least one of the weighing device and the pump, and adjusting operation of the fluid management system to operating the fluid management system in a second operating mode during the unstable condition. Operating the fluid management system in the second mode includes at least one of: a) using flow data received from the pump to calculate the fluid deficit, b) pausing operation of the pump, and c) transmitting an error message to a user.

Determining that the fluid management system is in the unstable condition may include obtaining a first weight measurement from the weighing device, wherein the first weight measurement corresponds to an amount of fluid in a fluid container at a first moment in time; obtaining a second weight measurement from the weighing device, wherein the second weight measurement corresponds to an amount of fluid in the fluid container at a second moment in time following the first moment in time; comparing the second weight measurement to the first weight measurement; determining that the fluid management system is in the unstable condition based on the comparison between the second weight measurement and the first weight measurement. The weighing device may be a supply fluid weighing device, the pump may be an inflow pump, and operating the fluid management system in the second mode may include using flow data received from the inflow pump to calculate the fluid deficit. Alternatively, the weighing device may be a waste fluid weighing device, the pump may be an outflow pump, and operating the fluid management system in the second mode may include pausing operation of the outflow pump.

The method may further include determining that the fluid management system is in a stable condition after adjusting operation of the fluid management system to operating the fluid management system in the second mode; and adjusting operation of the fluid management system to operating the fluid management system in the first mode after determining the stable condition.

The pump and the weighing device may be coupled to a fluid container, and determining that the fluid management system is in the unstable condition may include: operating the pump to pump fluid out of the fluid container; obtaining a plurality of fluid weight measurements during a predetermined time period from the weighing device while the pump dispenses fluid from the fluid container; obtaining a plurality of pump measurements during the predetermined time period from a measuring device coupled to the pump; calculating a first amount of fluid dispensed during the predetermined time period based on the obtained pump measurements; calculating a second amount of fluid dispensed during the predetermined time period based on the obtained fluid weight measurements; comparing the first amount to the second amount; and determining that a difference between the first amount and the second amount exceeds a predetermined difference limit, and thus that the fluid management system is in the unstable condition. In this embodiment, operating the fluid management system in the second mode may include pausing operation of the pump and transmitting the error message to the user.

Other and further aspects and features of the disclosed embodiments will become apparent from the ensuing detailed description in view of the accompanying drawings.

BRIEF DESCRIPTION OF THE DRAWINGS

The foregoing and other aspects of embodiments are described in further detail with reference to the accompanying drawings, wherein like reference numerals refer to like elements and the description for like elements shall be applicable for all described embodiments wherever relevant, and in which.

DETAILED DESCRIPTION

Disclosed herein is a fluid management system and a method for operating the fluid management system so that the fluid deficit can be more efficiently and effectively tracked. In particular, during a disruption to the system, the system automatically changes a mode of operation in order to more accurately track the fluid deficit during the disruption. Such a disruption may include changing a fluid supply bag, changing a waste fluid container, and/or having a blockage (such as an air bubble) in the fluid supply tubing. For example, a disruption occurs when a fluid supply bag is empty or nearly empty, and the empty supply bag is removed and replaced with a full supply bag. In another example, a disruption occurs when a waste fluid container that is full or nearly full is removed and replaced with an empty waste fluid container. In yet another example, a disruption occurs when the supply tubing becomes blocked, such as with an air bubble.

The fluid management system is configured to automatically detect when a disruption is occurring and to automatically switch to a different mode of operation during the disruption. The system is further configured to switch back to a normal mode of operation after the disruption is resolved. One purpose for the different mode of operation is so that the fluid deficit may be more accurately determined during the disruption. For example, during the changing of a supply fluid bag, the system may be configured to automatically switch from using weight data to using flow data to calculate the fluid deficit without pausing the procedure during the bag change. In another example, during the changing of a waste fluid container, the system may be configured to automatically turn off an outflow pump without pausing the procedure during the waste container change. In yet another example, when the system automatically detects that a supply tube is blocked (e.g., with an air bubble or the like), the system may automatically pause operations and a visual or audible notification may be transmitted to notify the user that such a blockage has occurred.

Figure 1:
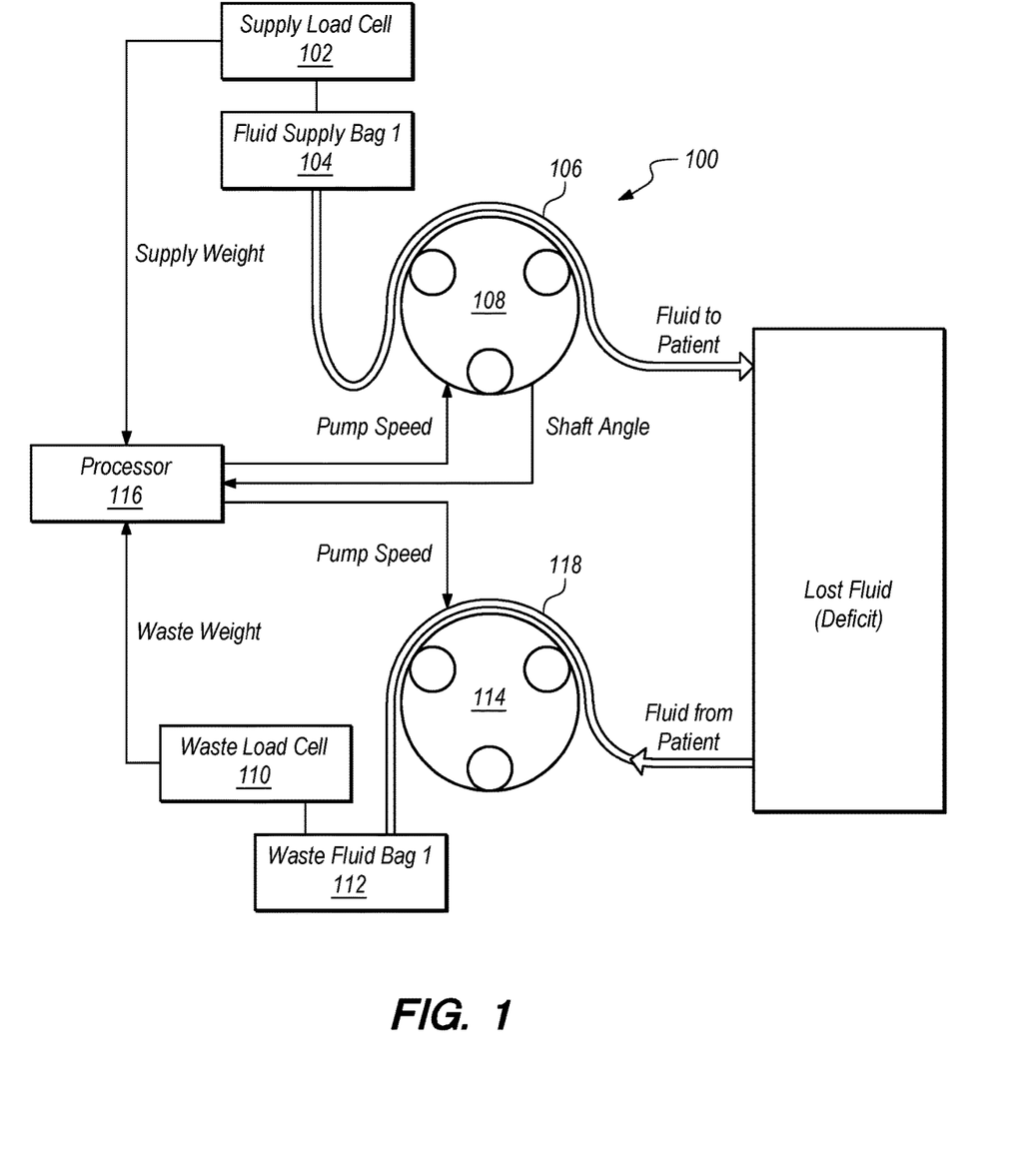
FIG. 1 is a block diagram of a fluid management system in accordance with an exemplary embodiment of the disclosed inventions.

The fluid management system 100 will now be described with reference to FIG. 1. The system 100 includes a supply fluid weighing device 102 coupled to a supply fluid container 104. The supply fluid weighing device 102 may be a load cell, or any other weight-sensitive device capable of producing a supply fluid weight signal indicative of the supply fluid weight. The supply fluid container 104 is typically a bag, but may alternatively be a bucket, bin, canister, or any other container suitable for holding the fluid to be supplied to a patient during a procedure. The supply fluid may be water, saline, or the like. The supply load cell 102 measures the weight of the supply bag 104. In yet another embodiment, the weight of the supply bag 104 may be measured by another means, such as a compression scale, electronic scale, or the like. An inflow pump 108 pumps the fluid from the supply fluid container 104 to the patient through supply fluid tubing 106.

The system 100 further includes a waste fluid weighing device 110 coupled to a waste fluid container 112. The waste fluid weighing device 110 may be a load cell, or any other weight-sensitive device capable of producing a waste fluid weight signal indicative of the waste fluid weight. The waste fluid container 112 may be a bag, bucket, canister, or any other container suitable for collecting waste fluid that is pumped from the patient with the outflow pump 114 through outflow tubing 118. The waste load cell 110 measures the weight of the waste fluid container 112. Alternatively, the weight of the waste fluid container 112 may be measured by another means, such as a compression scale, electronic scale, or the like.

The supply load cell 102 and the waste load cell 110 are coupled to a processor 116. The load cells 102, 110 provide weight data to the processor 116. The inflow pump 108 and the outflow pump 114 are also coupled to the processor 116, and the processor 116 is configured for controlling the pump speed for both of the pumps 108, 114. The inflow pump 108 is configured for providing flow data to the processor 116 so that the processor 116 can use the flow data to calculate the fluid deficit, if necessary. For example, the inflow pump 108 may include a pump shaft angle measurement device configured to detect the shaft angle and provide such data to the processor 116. Using this data, the processor 116 is able to calculate a fluid volume that has been provided to the patient. The pumps 108, 114 used in the system 100 are described in more detail in US Patent Application Publication 2017/0184088, which is hereby incorporated herein by reference in its entirety.

In general, under normal operating conditions, the fluid deficit of the system 100 is tracked by subtracting the total amount of fluid collected in the waste container 112 from the total amount of fluid dispensed from the supply container 104. The supply fluid amount and waste fluid amount are normally determined using the weight data provided by the load cells 102, 110. However, during the changing of a supply fluid container or a waste fluid container, the amount of the supply fluid or the waste fluid is in flux. For example, when one of the supply fluid bags 104 is empty or nearly empty and is removed from the system 100 and replaced with a full supply bag, the supply fluid amount increases rapidly and the amount of supply fluid added to the system 100 must be accounted for in the fluid deficit calculations. In the short amount of time during which the empty bag is being exchanged with a full bag, the supply fluid amount is temporarily unknown. Similarly, when a full or almost full waste fluid container 112 is replaced with an empty container, the waste fluid amount decreases rapidly and the amount of waste fluid removed from the system 100 must be accounted for in the fluid deficit calculations. In the short amount of time during which the full waste container is being replaced with an empty waste container, the waste fluid amount is temporarily unknown and cannot be calculated using the weight data provided by the waste load cell 110.

Figure 2:
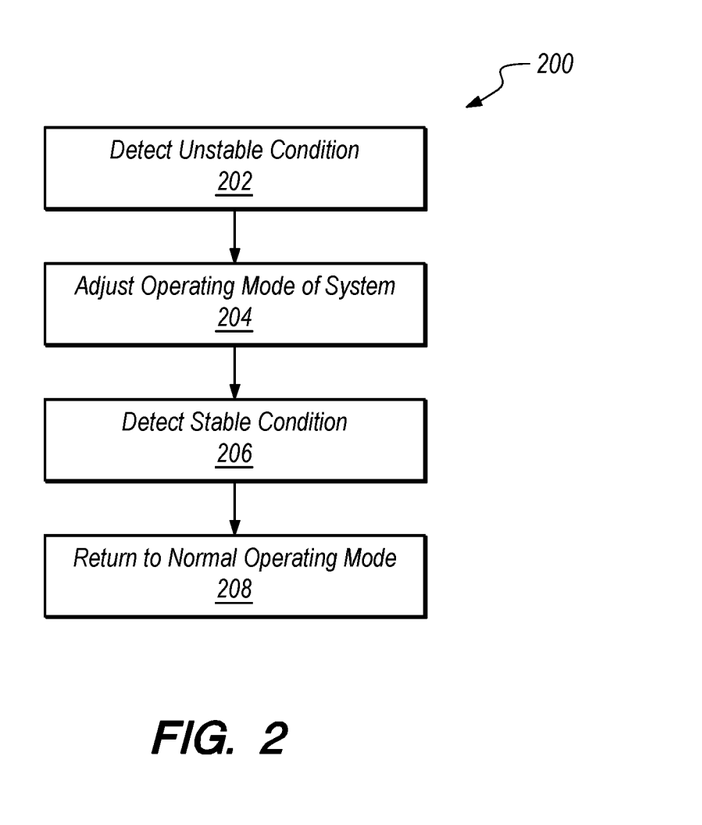
FIG. 2 is a flow chart of a method for operating the fluid management system depicted in FIG. 1.

As shown in FIG. 2, the method 200 for operating the system 100 includes a step 202 of detecting an unstable condition in the system 100. An unstable condition in the system 100 may be detected when a supply fluid bag is added or exchanged, when a waste fluid container is added or exchanged, or when there is a blockage in the supply tubing 106. After the unstable condition is detected, the operating mode of the system 100 is adjusted in step 204. The method 200 further includes a step 206 of detecting that the system 100 has returned to a stable condition, and a step 208 of returning the system 100 to normal operating mode. The step 204 of adjusting the operating mode of the system depends on what the unstable condition is. For example, if the unstable condition is that a supply fluid bag is being added or exchanged, then the operating mode of the system 100 is adjusted to calculate the supply fluid amount using flow data from the inflow pump 108 rather than weight data from the supply load cell 102. When the supply fluid bag change is complete, the system 100 is declared stable in step 206, and, in step 208, is returned to normal operating conditions where the supply fluid amount is calculated using the weight data from the supply load cell 102. In another example, if the unstable condition is that a waste fluid container is being added or exchanged, then the operating mode of the system 100 is adjusted in step 204 by pausing operation of the outflow pump 114. When the waste fluid container change is complete, then the system 100 is declared stable in step 206, and, in step 208, is returned to normal operating conditions where operation of the outflow pump 114 is resumed. In yet another example, if the unstable condition is that there is a blockage or air in the fluid supply tubing 106, then the operating mode of the system 100 is adjusted in step 204 by pausing operation of the system 100 and transmitting an error message to the user of the system 100. When the blockage is resolved, the system 100 is declared stable in step 206, and, in step 208, is returned to the normal operating conditions where operation of the system 100 is resumed, and transmission of the error message is halted.

In one example, when a supply fluid bag is being added or exchanged, the system 100 automatically detects an instability when the change between the current supply load cell measurement and the previous load cell measurement is relatively large. Under normal operating conditions, the maximum change in the supply weight occurs when the inflow pump 108 is operating at maximum speed. At maximum pump speed, the maximum change between the current supply load cell measurement and the previous supply load cell measurement may be, for example, between 2 and 6 grams (e.g., 4 grams). The system 100 automatically detects a disturbance when the change between the current supply load cell measurement and the previous supply load cell measurement is relatively large, such as between 30 and 70 grams (e.g., 50 grams). Upon detecting such a disturbance, the system 100 is configured to automatically switch to using flow data from the pump 108, rather than weight data from the load cell 102, to keep track of the fluid deficit during the disturbance. When the system 100 detects that the change between the current supply load cell measurement and the previous supply load cell measurement has stabilized (i.e., the fluid supply bag change is complete), the system 100 automatically adjusts the total supply fluid volume and switches back to normal operating conditions where the fluid deficit is tracked using weight data from the supply load cell 102.

Figure 3:
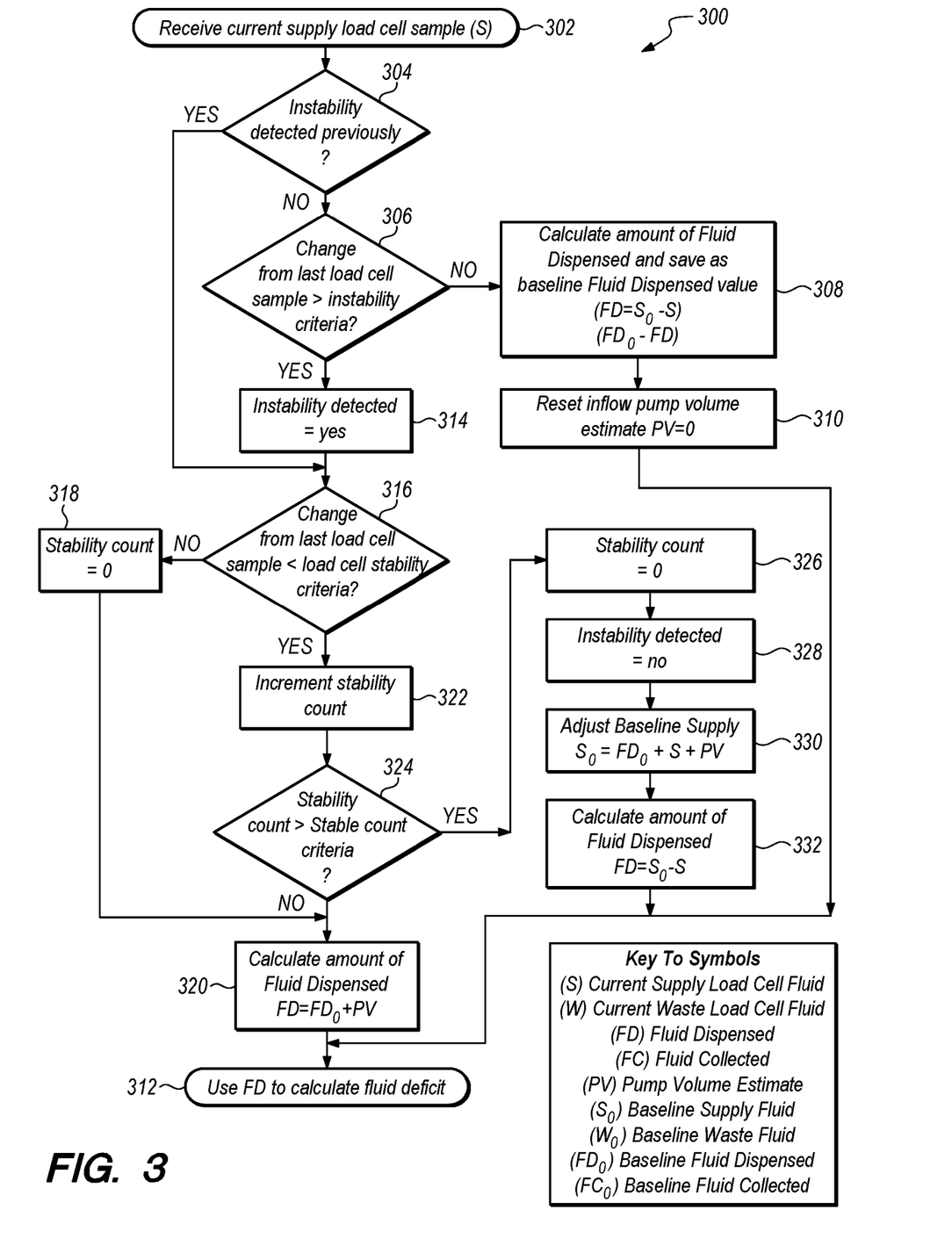
FIG. 3 is a flow chart of a method for operating the fluid management system of FIG. 1 during a supply bag exchange.

The supply fluid bag change procedure is discussed in more detail with reference to FIG. 3, which is a flow chart of a procedure 300 for determining the fluid deficit during a supply bag change. At the start of the method 300, a weight measurement (S) is received from the supply load cell 102 in step 302. In step 304, it is determined whether the system is currently stable or unstable. If an instability was not previously detected (i.e., the system is currently stable), then it is determined in step 306 whether the change between the current weight measurement (S) and the last weight measurement is greater than the instability criteria. The instability criteria is greater than the maximum amount of fluid than can be pumped during a sampling period, and is an amount that is chosen to be indicative of a supply bag change. In one example, the maximum amount of fluid that can be pumped during a sampling period is between 2 and 6 grams (e.g., 4 grams), and the instability criteria is between 30 and 70 grams (e.g., 50 grams). If the change is not greater than the instability criteria, then the system is still in a stable condition, and the amount of fluid dispensed is calculated and saved as the baseline amount of fluid dispensed in step 308. The amount of fluid dispensed is calculated by subtracting the current supply fluid amount (S, obtained in step 302) from the baseline supply fluid amount ($S_0$). The baseline supply fluid amount, $S_0$, is initially set to be equal to the amount of supply fluid initially provided before the procedure begins. As discussed in greater detail below, the baseline supply fluid amount, $S_0$, is adjusted each time a supply fluid container 104 is added or exchanged. Next, in step 310, the inflow pump volume estimate is reset to zero. The fluid-in and fluid-out amounts are volumes, but they may alternatively be other quantities, such as weight. As such, during stable operating conditions, the supply load cell measurement is used to calculate how much fluid has been pumped from the supply bags 104 into the patient. At the conclusion of the procedure 300, the fluid deficit is calculated in step 312 using the amount of fluid dispensed as determined in step 308.

If it is determined in step 306 that the change between the current weight measurement and the previous weight measurement is greater than the instability criteria, then the system is determined to be unstable in step 314. Alternatively, the system 100 may have previously been determined to be unstable in step 304. Once it is determined that the system is unstable (either by answering "yes" in step 304, or by determining that the change in load cell measurements is greater than the instability criteria in step 306), it is next determined in step 316 if the change between the current load cell sample and the previous load cell sample is less than the stability criteria. The stability criteria is slightly less than, or equal to, the maximum amount of fluid that may be pumped during a sampling period. For example, the stability criteria may be between 2 and 6 grams (e.g., 4 grams). If the change is greater than the stability criteria, then the system is still unstable and the stability count (which is discussed in greater detail below) is set to zero in step 318. Next, in step 320, the amount of fluid dispensed (FD) is calculated using flow data provided by the inflow pump 108. In particular, the amount of fluid dispensed (FD) is equal to the baseline fluid dispensed amount ($FD_0$) plus the amount of fluid (PV) that is estimated to have been pumped using the flow data. The flow volume may be determined using a known flow volume per rotation of the pump 108 and the rotational speed of the pump 108. As discussed above with reference to FIG. 1, the processor 116 receives flow data from the outflow pump 108 in the form of the shaft angle of the pump 108. Based on the shaft angle, the processor 116 is able to calculate the volume of the fluid that has been pumped within a given time frame.

In step 316, if the change is less than the stability criteria, than the stability count is incrementally increased in step 322. The stability count is a count of how many samples are determined to be within the stability criteria. Once a predetermined number of consecutive samples have been determined to be within the stability criteria, then the system may be declared stable. For example, if 5 load cell measurements in a row meet the stability criteria, then the system 100 may be declared to be stable. System stability is delayed by the stability count in order to ensure that the load cell reading remains stable before the system 100 returns to using the supply load cell 102 to calculate the volume of fluid dispensed. In this manner, detecting instability in the system 100 is a relatively quick procedure, while determining that the system 100 has returned to a stable condition takes more time. In step 324, it is determined whether the stability count is greater than a stability count criteria. If the stability count is not greater than the stability count criteria, then the number of stable samples has not yet been achieved, and the system is still in an unstable condition and the method 300 proceeds to step 320. In step 320, the amount of fluid dispensed (FD) is calculated by adding the pump volume estimate (PV) to the baseline amount of fluid dispensed ($FD_0$). If the stability count is greater than the stability count criteria in step 324, then the system 100 may be determined to be in a stable condition, and the stability count is reset to zero in step 326. Next, in step 328, it is determined that instability does not exist in the system. As such, the system is stable, and the baseline supply fluid amount ($S_0$) is adjusted in step 330 to include the added supply fluid amount and the estimated amount of fluid that was dispensed according to the pump volume estimate (PV). Specifically, the baseline supply fluid amount ($S_0$) is adjusted to be equal to the current supply fluid amount (S), plus the baseline amount of fluid dispensed ($FD_0$), plus the pump volume estimate (PV). Next, in step 332, the amount of fluid dispensed (FD) is calculated by subtracting the current supply fluid amount (S) from the baseline supply fluid amount ($S_0$). At the conclusion of the procedure 300, the fluid deficit is calculated in step 312 based on the amount of fluid dispensed (FD).

In another example, when a waste fluid container is being exchanged, the system 100 automatically detects an instability when the change between the between the current waste load cell measurement and the previous waste load cell measurement is relatively large. Under normal operating conditions, the maximum change in waste weight detected by the waste load cell 110 occurs when the waste containers 112 are being filled at a maximum rate. At this maximum fill rate, the maximum change between the current waste load cell measurement and the previous waste load cell measurement may be, for example, between 2 and 6 grams (e.g., 3.6-3.8 grams). The system 100 automatically detects a disturbance when the change between waste load cell measurement is relatively large (e.g., 50 grams). Upon detecting such a disturbance in the waste load cell measurements, the system 100 is configured to automatically pause operation of the outflow pump 114. The system 100 automatically detects that the change between waste load cell measurements has stabilized (i.e., the waste fluid container is exchange is complete) when the change between waste load cell measurements is within the stability range (between 2 and 6 grams or less) over several consecutive measurements. In this manner, detecting instability in the system 100 is a relatively quick procedure, while determining that the system 100 has returned to a stable condition takes more time. Upon determining that the waste load cell measurements have stabilized, the system 100 is configured to automatically resume operation of the outflow pump 114.

Figure 4:
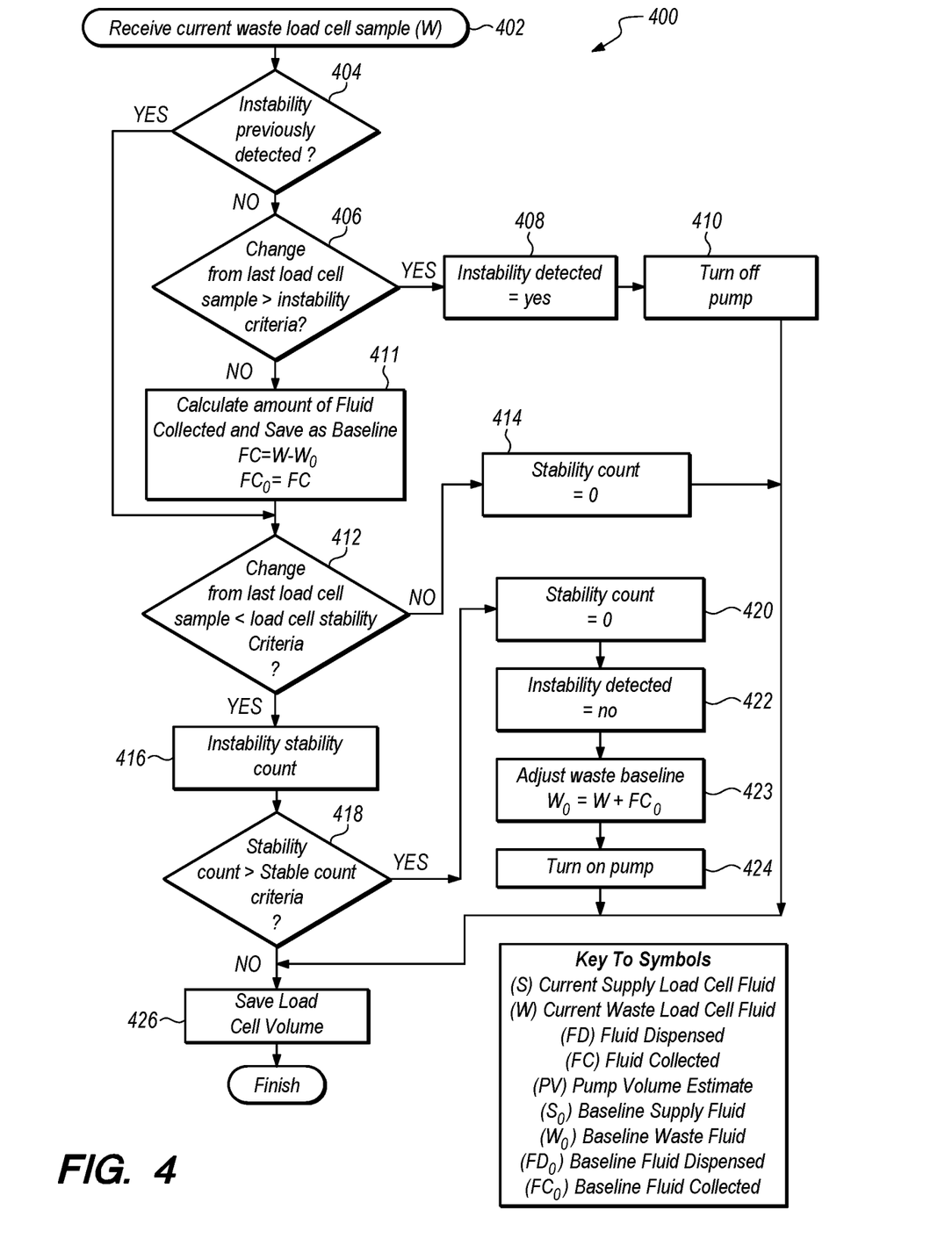
FIG. 4 is a flow chart of a method for operating the fluid management system of FIG. 1 during a waste container exchange.

The waste container exchange procedure is discussed in more detail with reference to FIG. 4, which is a flow chart of a procedure 400 for adjusting operation of the system 100 during a waste container exchange. At the start of the method 400, a current waste container weight measurement (W) is received from the waste load cell in step 402. In step 404, it is determined whether the system 100 is currently stable or unstable. If an instability was not previously detected (i.e., the system 100 is currently stable), then it is determined in step 406 whether the change between the current weight measurement and the last waste weight measurement is greater than the instability criteria. Similar to the method 300 discussed above with reference to FIG. 3, the instability criteria is greater than the maximum amount of fluid that can be collected during a sampling period, and is an amount that is chosen to be indicative of a waste container change. In one example, the maximum amount of fluid that can be collected during a sampling period is between 2 and 6 grams (e.g., 3.6-3.8 grams), and the instability criteria is between 30 and 70 grams (e.g., 50 grams). If the change is greater than the instability criteria, then instability is declared in step 408 and the outflow pump 114 is turned off in step 410. If the change is not greater than the instability criteria, then the amount of fluid collected (FC) is calculated and is saved as the baseline amount of fluid collected ($FC_0$) in step 411. In particular, the amount of fluid collected (FC) is equal to the current amount of waste fluid (W) minus a baseline amount of waste fluid ($W_0$). Prior to a waste container exchange, the baseline amount of waste fluid ($W_0$) is zero. When a waste container exchange occurs, the baseline amount of waste fluid ($W_0$) includes the amount of waste fluid that was removed from the system 100 when the full waste container was replace with an empty waste container.

Next, in step 412, it is determined whether the change between the current and previous load cell samples is less than the stability criteria. Similar to the method 300 discussed above with reference to FIG. 3, the stability criteria is slightly less than, or equal to, the maximum amount of fluid that may be collected during a sampling period. For example, the stability criteria may be between 2 and 6 grams. If it is determined in step 404 that an instability was previously detected (i.e., the system is currently declared unstable), then steps 406 and 411 are skipped and it is determined at step 412 if the change is less than the stability criteria. If the change is greater than the stability criteria, then the stability count is set to zero in step 414 and the load cell volume is saved in step 426 for comparison to the next waste load cell sample. In other words, if the change is greater than the stability criteria, then the system 100 is still not stable, so the count of stable samples is set to zero.

If it is determined in step 412 that the change is less than the stability criteria, then the stability count is increased incrementally in step 416. Next, in step 418, it is determined whether the stability count is greater than a stable count criteria. If the stability count is less than the stable count criteria in step 418, then the load cell volume is saved in step 426 and the procedure 400 is repeated for the next waste load cell measurement (W). If the stability count is greater than the stable count criteria, then the stability count is set to zero in step 420, the system is declared to be stable in step 422, the baseline waste amount is adjusted in step 423 to reflect the amount of waste fluid removed from the system 100, and the outflow pump 114 is turned on in step 424. In other words, if a predetermined number of consecutive samples have met the stability criteria, then the system 100 can be declared stable and the outflow pump 114 can be resumed. The baseline amount of waste fluid ($W_0$) is adjusted to be equal to the current amount of waste fluid (W) plus the baseline amount of fluid collected ($FC_0$). Next, the load cell volume is saved in step 426 and the procedure 400 is repeated for the next waste load cell sample.

In yet another example, the system 100 automatically detects a disturbance when the flow data received from the inflow pump 108 does not match the weight data received from the supply load cell 102. A difference between the flow data and the weight data that exceeds a threshold amount is indicative of a blockage or air in the supply tubing 106. Upon detecting such a disturbance, the system 100 automatically pauses the system and notifies the user of the disturbance. The notification may be in the form of a visual notification on a monitor, an audible alarm, or the like. When the blockage has been resolved, then the system 100 may resume operation.

Figure 5:
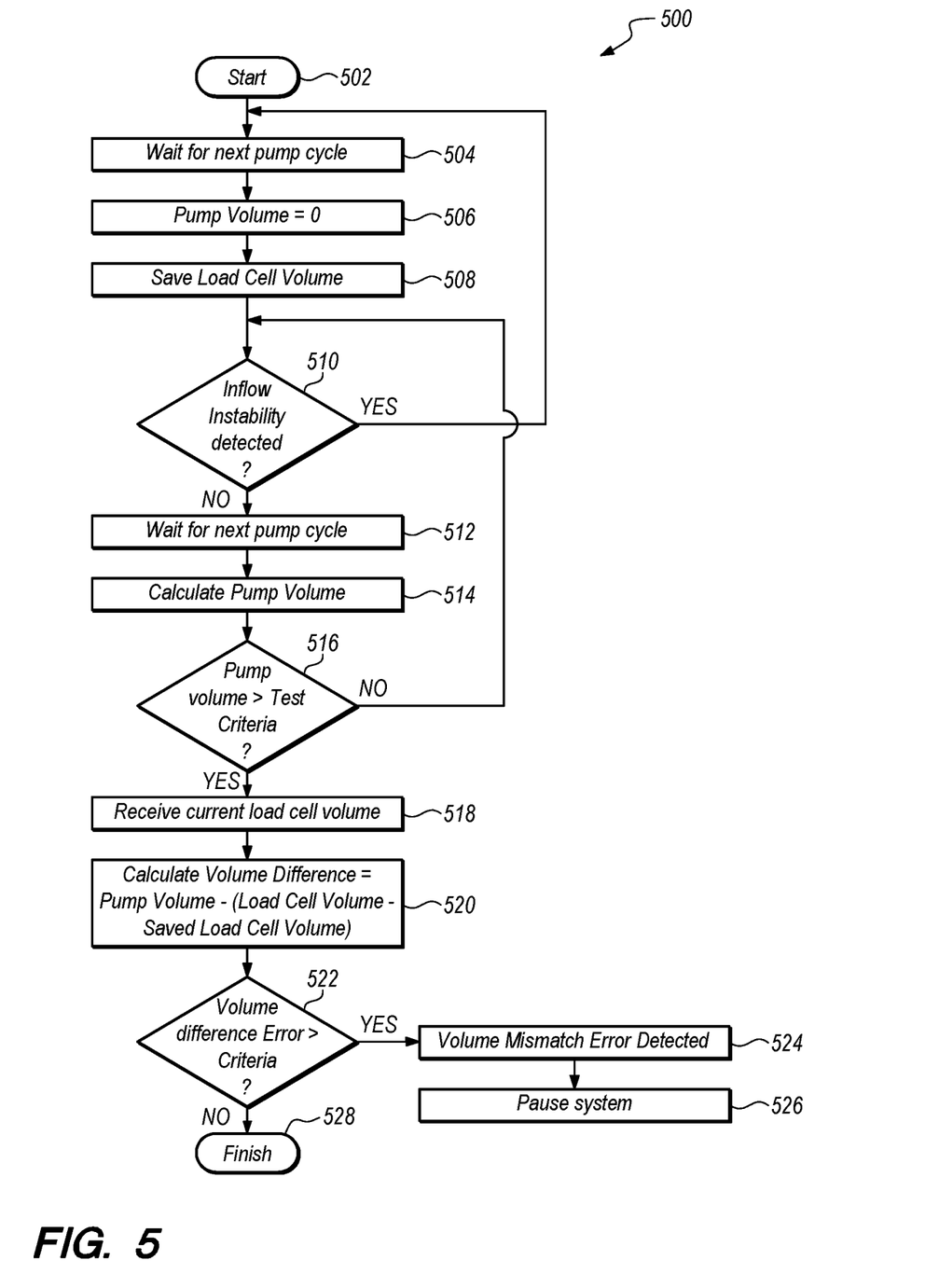
FIG. 5 is a flow chart of a method for operating the fluid management system of FIG. 1 during a blockage in the supply tubing.

The procedure 500 for detecting a supply tubing blockage and adjusting operation of the system 100 is discussed in greater detail with reference to FIG. 5. At the start 502 of the method 500, the next pump cycle has not been completed in step 504, and the pump volume is reset to zero in step 506. The load cell volume is saved in step 508. Next, in step 510, is it determined whether an instability has been detected. If an instability has been detected, steps 504-508 are repeated. In other words, steps 504-508 are repeated as long as the system is declared unstable. If an instability has not been detected (e.g, the system is currently declared stable), then the next pump cycle is completed in step 512 and the pump volume is calculated in step 514. If the pump volume is not greater than the test criteria in step 516, then steps 510-514 are repeated. The test criteria is a pump volume threshold value that is high enough to be compared to the load cell volume. The test criteria is approximately equal to, or slightly greater than, the volume of fluid that can be held in the supply tubing 106. A predetermined number of pump cycles must occur before the pump volume is high enough to be compared to the load cell volume. If the pump volume is greater than the test criteria in step 516, then a current load cell volume is received in step 518. Next, in step 520, the volume difference between the pump volume and the change in load cell volume is calculated. If the volume difference is greater than an error criteria in step 522, then an error is detected in step 524. The error criteria is a threshold value that is indicative of a blockage or air in the supply tubing 106. If the difference between the change in load cell volume and the calculated pump volume is higher than the error criteria, then there is most likely a blockage or air in the supply tubing 106. When an error is detected in step 524, the system is paused in step 526. All pumps are stopped until the blockage has been corrected. If the volume difference is within a predetermined range and is not greater than the error criteria in step 520, then the method 500 is completed at step 528.

While particular embodiments illustrating variations of the many aspects of the disclosed inventions have been disclosed and described herein, such disclosure is provided for purposes of explanation and illustration only. Thus, various changes and modifications may be made to the disclosed embodiments without departing from the scope of the claims. For example, not all of the components described in the embodiments may be necessary for any particular embodiment, and the disclosed inventions may include any suitable combination of the described components. Accordingly, the disclosed inventions should not be limited, except as set forth in the following claims, and their equivalents.

What is claimed is:

1. A fluid management system, comprising:
 a supply fluid weighing device configured for weighing a supply fluid container;
 an inflow pump configured to pump fluid out of the supply fluid container; and
 a processor coupled to each of the supply fluid weighing device and the inflow pump, wherein the processor is configured to
  determine whether the fluid management system is in a stable condition or an unstable condition,
  operate the fluid management system according to a first set of operating conditions when the system is in the stable condition, wherein the first set of operating conditions comprises using weight data obtained from the supply fluid weighing device to calculate the fluid deficit, and
  operate the fluid management system according to a second set of operating conditions that are different than the first set of operating conditions when the system is in the unstable condition, wherein operating the fluid management system according to the second set of operating conditions comprises
  receiving flow data from the inflow pump; and
  using the flow data to calculate a fluid deficit during the unstable condition.

2. The fluid management system of claim 1, wherein the supply fluid weighing device comprises one or more load cells.

3. The fluid management system of claim 1, wherein the processor is configured to obtain a first weight measurement from the supply fluid weighing device;

obtain a second weight measurement from the supply fluid weighing device after obtaining the first weight measurement;

determine a difference between the second weight measurement and the first weight measurement; and determine whether the system is in the stable condition or the unstable condition based upon the difference between the second weight measurement and the first weight measurement.

4. The fluid management system of claim 3, wherein the processor is configured to determine that the system is in the stable condition if the difference between the second weight measurement and the first weight measurement is within a predetermined limit.

5. The fluid management system of claim 4, wherein the processor is configured to determine that the system is in the unstable condition if the difference between the second weight measurement and the first weight measurement exceeds the predetermined limit.

6. The fluid management system of claim 1, wherein the supply fluid weighing device comprises one or more load cells, and wherein the processor is configured to obtain a first weight measurement from the supply fluid weighing device;

obtain a second weight measurement from the supply fluid weighing device after obtaining the first weight measurement;

determine a difference between the second weight measurement and the first weight measurement; and determine whether the system is in the stable condition or the unstable condition based upon the difference between the second weight measurement and the first weight measurement.

7. The fluid management system of claim 6, wherein the processor is configured to determine that the system is in the stable condition if the difference between the second weight measurement and the first weight measurement is within a predetermined limit, and wherein the processor is configured to determine that the system is in the unstable condition if the difference between the second weight measurement and the first weight measurement exceeds the predetermined limit.

8. A method for operating a fluid management system, the fluid management system comprising a supply fluid container, a supply fluid weighing device operatively coupled with the supply fluid container, an inflow pump configured to pump fluid out of the supply fluid container, a waste fluid container, a waste fluid weighing device operatively coupled with the waste fluid container, an outflow pump configured to pump fluid into the waste fluid container, and a processor operatively coupled to each of the supply fluid weighing device, the waste fluid weighing device, the inflow pump and the outflow pump, the method comprising:

determining whether the fluid management system is in a stable condition or an unstable condition;

operating the fluid management system according to a first set of operating conditions when the system is in the stable condition, wherein the first set of operating conditions comprises calculating the fluid deficit based on respective weight measurements received from the supply fluid weighing device and the waste fluid weighing device; and operating the fluid management system according to a second set of operating conditions that are different than the first set of operating conditions when the system is in the unstable condition, wherein operating the fluid management system according to the second set of operating conditions comprises receiving flow data from the inflow pump, and using the flow data to calculate a fluid deficit during the unstable condition.

9. The method of claim 8, wherein determining whether the system is in the stable condition or the unstable condition comprises receiving a current weight measurement from the supply fluid weighing device;

comparing the current weight measurement to a previous weight measurement received from the supply fluid weighing device; and determining that the system is in the stable condition if the difference between the current weight measurement and the previous weight measurement is within a predetermined limit.

10. The method of claim 9, further comprising determining that the system is in the unstable condition if the difference between the current weight measurement and the previous weight measurement exceeds the predetermined limit.

11. The method of claim 8, wherein determining whether the system is in the stable condition or the unstable condition comprises receiving a current weight measurement from the supply fluid weighing device;

comparing the current weight measurement to a previous weight measurement received from the supply fluid weighing device; and determining that the system is in the stable condition if the difference between the current weight measurement and the previous weight measurement is within a predetermined limit.

12. The method of claim 11, further comprising determining that the system is in the unstable condition if the difference between the current weight measurement and the previous weight measurement exceeds the predetermined limit.

* * * * *